United States Patent [19]

Naito et al.

[11] Patent Number: 4,591,497

[45] Date of Patent: May 27, 1986

[54] ODOR-REMOVING AND DEODORIZING COMPOSITION EMPLOYING A HYDROLYSATE OF KERATIN MATERIAL

[75] Inventors: Sachio Naito, Tokyo; Toshiyuki Nemoto, Ichikawa, both of Japan

[73] Assignee: Kao Corporation, Tokyo, Japan

[21] Appl. No.: 630,341

[22] Filed: Jul. 13, 1984

Related U.S. Application Data

[63] Continuation of Ser. No. 416,618, Sep. 10, 1982, abandoned.

[30] Foreign Application Priority Data

Sep. 18, 1981 [JP] Japan .................. 56-147456

[51] Int. Cl.$^4$ ............... A61L 9/01; A61L 9/04
[52] U.S. Cl. ........................... 424/43; 424/76
[58] Field of Search .................. 424/43, 76

[56] References Cited

FOREIGN PATENT DOCUMENTS 715546  9/1954  United Kingdom .
1584693  2/1981  United Kingdom .
1584694  2/1981  United Kingdom .

OTHER PUBLICATIONS

Taiyo; Chem. Abst., vol. 93, (1980) 237284d.

*Primary Examiner*—Allen J. Robinson
*Attorney, Agent, or Firm*—Oblon, Fisher, Spivak, McClelland & Maier

[57] ABSTRACT

This invention discloses a novel odor-removing and deodorizing composition which comprises as its effective component a hydrolysate of keratin material. The hydrolysis of keratin material may be effected by any known methods using acid, alkali or enzyme. The composition according to the invention can be used in any known forms by treating the keratin hydrolysate to be an odor-removing base by usual manners. The composition effectively acts on mercaptan and hydrogen sulfide with which it has been considered difficult to remove their odors and shows little mucous stimulativeness.

10 Claims, No Drawings

ODOR-REMOVING AND DEODORIZING COMPOSITION EMPLOYING A HYDROLYSATE OF KERATIN MATERIAL

This is a continuation of application Ser. No. 416,618, filed Sept. 10, 1982 now abandoned.

BACKGROUND OF THE INVENTION

1. Field of the Invention

This invention relates to an odor-removing and deodorizing composition and more particularly, to a composition of the just-mentioned type comprising hydrolysates of keratin materials.

2. Description of the Prior Art

Offensive odors emitted from refuse boxes, water closets and the like involved in places of human activity such as, for example, ordinary homes, business facilities and public service and particularly those of mercaptan, hydrogen sulfide and the like which have been considered difficult in removing their odors are highly desired to be advantageously removed or masked and deodorized. Also during the course of permanent waving, there is generated a bad smell such as of mercaptan ascribed to the decomposition of thioglycol contained in chemicals and keratin in the hair on the way of the treatment, often causing one to feel objectionably.

A number of methods of removing the offensive odor or smell have heretofore been proposed and may broadly be classified into four categories including an odor-removing neutralization method, an odor-removing adsorption method, an odor-removing masking method and an odor-removing biochemical method. However, these methods have all the following disadvantages and are not necessarily satisfactory.

(1) Neutralization Method

This is a method of neutralizing acidic or basic materials giving off bad odor by application with basic or acidic odor-removing bases. This method is effective for local removal of odor but has the disadvantage, when the odor over a wide sphere is removed, that a large quantity of odor-removing bases is required and the efficacy of bases does not develop unless excess neutralization is effected, thus this method being not practically useful in most cases. Moreover, the vital drawback of the method is that neutral offensive odors, e.g. a putrid smell ascribed to mercaptan, cannot be removed.

(2) Adsorption Method

This is a method of adsorbing offensive odors on porous materials such as active carbon but has the disadvantages that the diffusion of offensive odors into adsorbents is rate-limiting and the adsorbent does not have effect on removal of odor over a wide area, that it takes long time before an adsorption equilibrium is reached and it is not necessarily easy for the equilibrium system to lower the concentration below a threshold value of offensive odor, and that adsorbents do not show activity with respect to all the types of offensive odors.

(3) Masking Method

This is a method of merely masking offensive odors with perfumes and thus the origin of offensive odor is not removed substantially, so that this method is not a substantial odor-removing method.

(4) Biochemical Method

This is a method of preventing emission of bad smells by lowering the activity of microorganisms with use of bacteriostatics or bactericides, but the method is preventive and does not give any effect on once emitted offensive odors.

As having described above, the currently employed odor-removing methods are not satisfactory for all origins of offensive odors and particulary for mercaptan and hydrogen sulfide. In this connection, there have recently been reported deodorizing bases which are effective for mercaptan and hydrogen sulfide but almost all of these bases are highly stimulative against mucous membranes such as of eyes, nose, throat and the like and cannot be applied actually.

SUMMARUY OF THE INVENTION

Under these circumstances, the present invention have made a study to find out odor-removing bases which effectively act on mercaptan and hydrogen sulfide with which it has been considered difficult to remove their odors or deodorize and which show little mucous stimulativeness and found that hydrolysates of keratin materials satisfy the above requirement.

That is, the present invention provides a novel odor-removing and deodorizing composition which comprises as its effective component a hydrolysate of keratin material.

DETAILED DESCRIPTION OF THE INVENTION AND PREFERRED EMBODIMENTS

The hydrolysates of keratin material (hereinafter referred to as "keratin hydrolysate(s)) used in the present invention are obtained by hydrolyzing keratin materials.

The starting keratin materials are, for example, animal hairs, human hair, feathers, nails, horns, hooves, scales and the like, among which wool, human hair and feathers are most preferable. These keratin materials may be subjected to the oxidation or reduction reaction as they are, or may be cut or reduced into pieces or may be subjected to pretreatments such as washing and defatting as desired.

The hydrolysis of keratin material may be effected by any known methods without limitation. Examples of the methods are as follows.

(1) Hydrolysis with Acid

Examples of acids include inorganic acids such as hydrochloric acid, sulfuric acid, phosphoric acid, nitric acid, hydrobromic acid and the like, and organic acids such as acetic acid, formic acid, oxalic acid and the like.

The hydrolysates obtained by the acid hydrolysis do not undergo any changes other than hydrolysis at polypeptide chains of keratin, so that better results are obtained than in the case of hydrolysis with alkali.

(2) Hydrolysis with Alkali

Examples of alkalis include inorganic alkalis such as sodium hydroxide, potassium hydroxide, lithium hydroxide, barium hydroxide, sodium carbonate, potassium carbonate, lithium carbonate, sodium silicate, borax and the like.

(3) Hydrolysis with Enzyme

Examples of enzymes include acidic proteinases such as pepsin, protease A, protease B and the like, and neutral proteinases such as papain, promeline, thermolycin, trypsin, pronase, chymotrypsin and the like.

The hydrolysates obtained by these hydrolysis reactions should preferable have an average molecular weight of from 200 to 5,000. The disulfide bonds in the keratin hydrolysates should favorably be left in amounts as great as possible. To this end, it is recommended to use a keratin material of high purity and to effect the hydrolysis under mild conditions.

The odor-removing and deodorizing composition according to the present invention can be used in any known forms by treating the keratin hydrolysate to be an odor-removing base by usual manners, including liquids obtained by dissolving the hydrolysate in solvents or emulsifying it using surface active agents; aerosols obtained by filling the liquids in a spray container along with an injector; gel-like solids mixed with natural or synthetic gel bases such as agar-agar, carrageenan, polyethylene glycol and the like; solids in which the hydrolysate is absorbed in paper or porous materials or is incorporated in synthetic resins such as polyethylene; and powders in which the hydrolysate is admixed with powdery, inorganic materials such as silica, perlite and the like.

If necessary, solvents, surface active agents, acidic materials such as hydrochloric acid, phosphoric acid, citric acid, malic acid, tartaric acid and the like, alkaline materials such as sodium hydroxide, triethanolamine, basic amino acids and the like, bactericides, perfumes; colorants and the like may be further added to the composition of the invention.

In the production of the odor-removing and deodorizing agents, there are used as a solvent alcohols or glycols such as ethanol, isopropanol, propylene glycol, polyethylene glycol, diethylene glycol, triethylene glycol and the like, or deionized water. Examples of the surface active agents include anionic active agents such as higher alcohol sulfates, alkylarylsulfonates, soaps of fatty acids or resin acids, polyoxyethylenealkyl or alkylphenyl ether sulfates, alkylsulfosuccinates, alkylsulfonates, α-olefinsulfonates and the like, nonionic active agents such as polyoxyethylenealkyl phenyl ethers, polyoxyethylene alkyl ethers, polyoxyethylene sorbitan fatty acid esters, polyoxyethylene stearate, glycerol fatty acid esters, ethylene oxide adducts or castor oil or lanolin and the like, and anionic and amphoteric active agents such as quaternary ammonium salts, higher alcohol betaine and the like. Examples of the bactericides (antiseptics) include parahydroxyalkyl benzoates (parabens), sorbic acid or its potassium salt, dehydroacetic acid or its sodium salt, sodium propionate, and anionic and amphoteric active agents.

The amount of the odor-removing and deodorizing composition of the invention varies depending on the intensity and type of offensive odor and is determined so that the concentration of the keratin hydrolysate is generally in the range of over 0.01 wt% (hereinafter referred to simply as %), inclusive, preferably over 0.1%, of the system to be treated. Accordingly, the amount of the keratin hydrolysate in the odor-removing and deodorizing composition is in the range of 0.1–10%, preferably 0.5–5%.

The odor-removing and deodorizing composition of the invention can be used over a wide range of pH by adjusting with acidic or alkaline materials to a pH of 0.5–10, preferably 1–8. Accordingly, when the composition is adjusted in pH to an acidic range of, for example, 1–3, it is possible to remove not only offensive odors of mercaptan and hydrogen sulfide but also the odor of ammonia.

The present invention is described by way of references and examples, which should not be construed as limiting the present invention thereto.

Reference: Preparation of Hydrolysates of Keratin Materials (a) 10 g of wool fibers were immersed in 300 g of a 75% phophoric acid aqueous solution and hydrolyzed at a temperature of 120°–130° C. for 5 hours. The reaction solution was cooled and filtered to remove insoluble matters therefrom, after which 4–5 times by volume of water was added and insoluble matters were further removed by centrifugation. Then, calcium carbonate or barium hydroxide was added to adjust the pH to 6.7, followed by collecting the resulting precipitate by filtration and drying to obtain 8.0 g of a hydrolysate with a molecular weight of 1,500.

(b) 100 g of feathers were heated in an autoclave by means of a superheated steam of 6 kg/cm$^2$ and 240° C. for 6 minutes and released abruptly into the air to obtain a porous puffed product. This puffed product was reduced into pieces and admixed with 3 liters of 0.3N caustic soda, followed by hydrolysis at 60° C. for 18 hours, neutralizing with 1N hydrochloric acid and filtering the reaction solution. The resulting filtrate was subjected to the ultrafiltration using a membrane with a fractional molecular weight of 500 to remove sodium chloride therefrom, with the aqueous solution of the keratin hydrolysate being concentrated, followed by freeze drying to obtain 7.2 g of the keratin hydrolysate. The molecular weight of the hydrolysate determined by the gel filtration technique was 1,800.

EXAMPLE 1

An odor-removing and deodorizing composition of the following composition was prepared and its odor-removing effect was examined.

The odor-removing effect was determined as follows. That is, 0.05 ml of a methyl mercaptan standard solution* was placed in a 100 ml Erlenmeyer flask as an offensive odor source, into which was immediately dropped 0.5 ml of the composition, followed by tightly sealing and keeping at 20° C. for 5 minutes. Then, the concentration of the methyl mercaptan was measured by the Kitagawa detector tube and after standing for 5 minutes, the odor in the flask was evaluated by 5 panel members.

* Methyl mercaptan standard solution:

Methyl mercaptan standard solution for testing bad smell substances (Wako Junyaku Ind. Co., Ltd: content 1 μg/1 μl (benzene solution))
Composition:

|  | Composition A (Product of Invention) | Composition B (Comparative Product) |
|---|---|---|
| Hydrolysate of Keratin (obtained in Reference (a)) | 1.5 (%) | —(%) |
| Glyoxal | — | 1.0 |
| Water | balance | balance |

Results:

TABLE 1

|  | Concentration of methyl mercaptan (after 5 minutes) | Sensory Evaluation (after 10 minutes) |
| --- | --- | --- |
| Composition A | 5 ppm | odor of benzene |
| Composition B | 90 ppm | odors of methyl mercaptan and benzene |

EXAMPLE 2

An odor-removing and deodorizing composition of the formulation indicated in Table 2 was prepared and sprayed for 5 seconds in a one liter beaker in which had been placed 1 ml of mercaptoethanol and 96 ml of purified water to examine its odor-removing effect. The effect was judged by organoleptically evaluating odors in the beaker by 5 panel members 3 minutes after the spraying.

TABLE 2

|  | Composition C (Product of Invention) | Composition D (Comparative Product) |
| --- | --- | --- |
| Keratin hydrolysate (obtained in Reference (b)) | 1.5 (%) | —(%) |
| Ethyl alcohol | 3.0 | 3.0 |
| Water | 55.5 | 56.0 |
| Glyoxal | — | 1.0 |
| Injector for aerosol (Flon 12) | 40.0 | 40.0 |
| Odor-removing effect | No odor of mercaptoethanol. | Intense odor of mercaptoethanol. |

EXAMPLE 3

An odor-removing and deodorizing composition of the formulation indicated in Table 3 for use in permanent wave treatment was prepared and its effect was examined. The results are shown in Table 4.

Composition:

TABLE 3

|  | Composition E (Product of Invention) | Composition F (Comparative Product) | Composition G (Comparative Product) |
| --- | --- | --- | --- |
| Keratin hydrolysate (obtained in Reference (a)) | 1.0 (%) | —(%) | —(%) |
| Alkali hydrolysate of colagen (molecular weight of about 2,000) | — | 1.0 | — |
| Malic acid | pH adjusted to 2 | pH adjusted to 2 | pH adjusted to 2 |
| Water | balance | balance | balance |

Test method:

4 tresses of human hairs each having a weight of 10 g and a length of 20 cm were each immersed in 100 ml of first agent for permanent wave (waving lotion) for 15 minutes to conduct the perm treatment. Thereafter, the four tresses were removed, lightly squeezed and applied with 5 ml of the odor-removing and deodorizing composition, followed by organoleptically evaluating the effect by 10 panel members.

For control, the treated tress was washed with running water for 10 seconds without use of any odor-removing and deodorizing composition and its effect was also judged.

| (First Agent of Permanent Wave (Waving lotion)) | |
| --- | --- |
| Ingredients | Wt % |
| Ammonium thioglycollate | 7.0 |
| EDTA-2Na salt | 0.5 |
| 28% aqueous ammonia | pH adjusted to 9.0 |
| Monolauric acid polyoxyethylene sorbitan (20 E.O.) | 1.0 |
| Perfume | small amount |
| Water | balance |

Results:

| Odor-removing deodorizing composition | | Evaluation Results |
| --- | --- | --- |
| Composition E | | No odors of thioglycollic acid and ammonia. |
| Composition F | Δ | Little odor of ammonia is left with an intense odor of thioglycollic acid. |
| Composition G | Δ | Little odor of ammonia is left with an intense odor of thioglycollic acid. |
| Control | X | Intense odors of thioglycollic acid and ammonia. |

EXAMPLE 4

An odor-removing and deodorizing composition of the formulation indicated in Table 5 for use in permanent wave treatment was prepared and three females with a hair length of about 20 cm as subjects were each actually permanent waved. The odor-removing and deodorizing effect on the emitted offensive odors was evaluated. The results are shown in Table 6.

Composition:

|  | Composition H (Product of Invention) | Composition I (Comparative Product) |
| --- | --- | --- |
| Keratin hydrolysate (obtained in reference (b)) | 2.0 (%) | — (%) |
| Citric acid | pH adjusted to 3.0 | pH adjusted to 3.0 |
| Polyoxyethylene sorbitan monooleate (20 E.O.) | 0.1 | 0.1 |
| Perfume | 0.05 | 0.05 |
| Methylparaben | 0.1 | 0.1 |
| Disodium EDTA | 0.3 | 0.3 |
| Water | balance | balance |

Test Method:

The hair wound about a rod was applied with 80 ml of a commercially available the first agent for permanent wave (waving lotion) containing as its chief component ammonium thioglycollate and allowed to stand for 15 minutes.

Then, (1) Subject A was washed with running water for 1 minute, (2) Subject B was applied with 30 g of the present composition indicated in Table 5, and (3) Subject C was applied with 30 g of the comparative product indicated in Table 5.

The odors of the respective hairs were evaluated by 5 panel members.

Thereafter, 100 ml of a second agent for the permanent wave (neutralizer) was applied to each of the hairs, which was allowed to stand for 15 minutes, and washed with water for 2 minutes, followed by evaluation by the expert panel.

Results:

TABLE 6

| | After Treatment with First Agent (Waving lotion) | | After Permanent Wave Treatment | |
|---|---|---|---|---|
| Subject A | X | (Offensive odors of thioglycollic acid and ammonia) | X | (Offensive odors of thioglycollic acid and ammonia) |
| Subject B | | | | |
| Subject C | X | (Offensive odor of thioglycollic acid) | X | (Offensive odor of thioglycollic acid) |

What is claimed is:

1. An odor-removing and deodorizing composition comprising:
   (a) 0.1 to 10% of a keratin hydrolysate having an average molecular weight of about 200–5000 which is obtained by subjecting a material selected from the group consisting of wool, animal hair, feathers, nails, horns, hooves and scales to a hydrolysis step with an inorganic acid or an inorganic alkali, at an appropriate temperature for sufficient time to obtain said keratin hydrolysate; said acid hydrolysis being carried out at between about 120° to 130° C., and said alkaline hydrolysis being carried out about 60° C.; and
   (b) an additive.

2. The odor removing and deodorizing composition of claim 1 in liquid form, wherein an acidic or alkaline material is added to obtain a pH of between about 0.5–10.

3. The composition of claim 2 wherein the pH is between 1 and 8.

4. The composition of claim 3 wherein the pH is between 1 and 3.

5. The composition of claim 1 wherein said additive is a solvent, surface active agent, aerosol, acidic or alkaline material, bactericide, perfume, colorant, gel or gel-like material or inorganic powder.

6. A method of removing odor from a source of offensive odor comprising exposing said offensive odor source to an effective amount of the composition of claim 1.

7. The method of claim 6 wherein the acid hydrolysis is carried out at between about 120° to 130° C. for about 5 hours.

8. The method of claim 6 wherein the alkaline hydrolysis is carried out at about 60° C. for about 18 hours.

9. The method of claim 8 further comprising prior to the alkaline hydrolysis step:
   subjecting said material to a puffing step; and
   cutting said puffed material into pieces.

10. The method of claim 16, wherein the odor from a source of offensive odor is an offensive odor generated by the composition of thioglycol contained in chemicals used in the process of permanent waving as well as in keratin in the hair.

* * * * *